(12) United States Patent
Qi et al.

(10) Patent No.: US 10,786,599 B2
(45) Date of Patent: Sep. 29, 2020

(54) IMPLANTABLE MEDICAL INSTRUMENT PREFORM, IMPLANTABLE MEDICAL DEVICE AND PREPARATION METHOD THEREOF

(71) Applicant: Lifetech Scientific (Shenzhen) Co., Ltd., Shenzhen (CN)

(72) Inventors: Zuqiang Qi, Shenzhen (CN); Xiaole Jia, Shenzhen (CN); Zhou Chen, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 155 days.

(21) Appl. No.: 15/579,336

(22) PCT Filed: May 26, 2016

(86) PCT No.: PCT/CN2016/083420
§ 371 (c)(1),
(2) Date: Dec. 4, 2017

(87) PCT Pub. No.: WO2017/000712
PCT Pub. Date: Jan. 5, 2017

(65) Prior Publication Data
US 2018/0185545 A1    Jul. 5, 2018

(30) Foreign Application Priority Data
Jun. 30, 2015 (CN) .......................... 2015 1 0375689

(51) Int. Cl.
*A61L 27/34* (2006.01)
*A61L 27/04* (2006.01)
(Continued)

(52) U.S. Cl.
CPC .............. *A61L 27/34* (2013.01); *A61F 2/01* (2013.01); *A61L 27/04* (2013.01); *A61L 27/42* (2013.01);
(Continued)

(58) Field of Classification Search
None
See application file for complete search history.

(56) References Cited

U.S. PATENT DOCUMENTS

| 7,899,552 B2 * | 3/2011 | Atanasoska | A61N 1/05 607/122 |
|---|---|---|---|
| 8,771,343 B2 * | 7/2014 | Weber | A61F 2/91 623/1.46 |

(Continued)

FOREIGN PATENT DOCUMENTS

| CN | 1628863 A | 6/2005 |
|---|---|---|
| CN | 1569270 B | 6/2011 |

(Continued)

OTHER PUBLICATIONS

International Search Report for corresponding PCT/CN2016/083420 dated Sep. 5, 2016.

*Primary Examiner* — Todd J Scherbel
(74) *Attorney, Agent, or Firm* — Raymond Sun

(57) ABSTRACT

Provided are an implanted medical device (1) and preparation method thereof, and an implanted medical device preform for preparing the implanted medical device (1). The implanted medical device (1) comprises a metal basal body (21) and a polymer film layer (22) covering the surface of the metal basal body (21) and preventing endothelium growth and covering, wherein at least a part of the surface of the metal basal body (21) is provided with a surface-modified layer (211) which contains doped ions, and the metal basal body (21) is connected to the polymer film layer (22) by the doped ions. Since the metal basal body (21) may (Continued)

be bonded to the polymer film layer (22) by the doped ions, the polymer film layer (22) is unlikely to separate during delivery, therefore effectively preventing endothelium growth and covering in vivo.

9 Claims, 2 Drawing Sheets

(51) Int. Cl.
*A61L 27/50* (2006.01)
*A61F 2/01* (2006.01)
*A61L 27/42* (2006.01)
*A61M 31/00* (2006.01)

(52) U.S. Cl.
CPC ......... *A61L 27/50* (2013.01); *A61F 2002/018* (2013.01); *A61F 2210/0014* (2013.01); *A61F 2230/006* (2013.01); *A61F 2240/001* (2013.01); *A61L 2400/18* (2013.01); *A61L 2430/36* (2013.01); *A61M 31/00* (2013.01)

(56) References Cited

U.S. PATENT DOCUMENTS

| 2009/0099634 A1* | 4/2009 | Atanasoska | A61N 1/05 |
| | | | 607/121 |
| 2009/0118813 A1* | 5/2009 | Scheuermann | A61F 2/91 |
| | | | 623/1.15 |

FOREIGN PATENT DOCUMENTS

| CN | 101347634 B | 10/2012 |
| JP | 11313884 | 11/1999 |
| RO | 127024 A2 | 1/2012 |

* cited by examiner

IMPLANTABLE MEDICAL INSTRUMENT PREFORM, IMPLANTABLE MEDICAL DEVICE AND PREPARATION METHOD THEREOF

TECHNICAL FIELD

The present invention relates to the field of medical devices, and more particularly to an implanted medical device preform, an implanted medical device, and preparation method thereof.

BACKGROUND ART

Pulmonary embolism (PE) is a common disease with high mortality, and statistics show that untreated pulmonary embolism mortality rate is 20%-30%. New cases per year account for about 0.2% of the total population, and there are about 2.7 million new patients each year when calculated with the 1.35 billion population in China as a whole. A vena cava filter (hereinafter referred to as the filter) was clinically proven to reduce the incidence of pulmonary embolism. The filters are usually made of metal and are divided into permanently implanted filters and temporary filters. Regardless of the type of filter, after it has been implanted into the vena cava for a period of time, due to the fact that it contacts the blood vessel endothelium, endothelium growth and covering, such as protein adsorption and platelet adhesion, may be caused, and thrombosis will eventually be formed, leading to venous vessel blockage or a recurrence of pulmonary embolism. Especially for the temporary filters, the above-mentioned endothelium growth and covering may also damage the endangium while increasing the difficulty of removal.

A polymer film layer preventing endothelium growth and covering is applied on the surface of the metal basal body of the filter, such as a polyethylene glycol-like (PEG-like) film, which is typically less than 3 microns thick and can improve the bioadhesion resistance of the surface of the filter. Interaction of the surface of the filter with the inner wall of the blood vessel and the blood is inhibited to reduce the growth and encapsulation of the vascular endothelial cells on the surface of the filter, and possible coagulation for forming thrombosis, thereby enabling the filter to remain fully open and further achieving good recovery performance of the filter.

However, the polymer film layer (hereinafter referred to as a film) and the metal basal body of the filter (hereinafter referred to as a basal body) are generally connected by small-acting forces, such as mechanical bonding and van der Waals forces. When the film directly covers the surface of the filter, the film cannot be firmly and effectively attached to the metal surface, and will easily fall off from the metal surface. This is especially important for filters. Unlike other implanted medical devices, such as occluders or stents, when the filter is ready for delivery, it is connected to the delivery steel cable and is preloaded within a guide sheath, usually a smaller 6F guide sheath. During surgery, before the filter is implanted, it is required to be loaded into a delivery sheath, and the filter is implanted into the body through the delivery sheath. During the process of retracting the filter into the delivery sheath, with the filter being compressed by forces, various parts of the filter will suffer from strong extrusion and friction, and the filter will inevitably be in friction with the inner wall of the delivery sheath when it is delivered in a delivery sheath having a length of about 550 mm. If a binding force between the film and the basal body is insufficient, the film will easily fall off or separate, and may even be separated from the basal body in large pieces after a series of extrusion and friction.

The surface of the metal basal body after the separation of the film will be in direct contact with the inner wall of the blood vessel, and the endothelial cells tend to grow and encapsulate the metal surface, which is not conducive to recovery. In addition, the separated films may travel to the lungs with the blood flow to obstruct the lung capillaries, or for patients with heart defects, the films could possibly travel into the brain through atrial septal defects to obstruct the brain blood vessels, all of which can be life-threatening. Thus, for an implanted medical device including polymer film layers and the metal basal body, it is significant to improve the adhesion between the film and the surface of the metal basal body to prevent the film from separating during delivery and after implantation.

SUMMARY OF THE INVENTION

The technical problem to be solved by the present invention is to provide an implantable medical device and preparation method thereof, and an implantable medical device preform for preparing the implantable medical device, in regard to the defect that the polymer film layer preventing endothelium growth and covering on the surface of the implanted medical device of the prior art cannot be firmly bound to the metal basal body.

The technical solution of the present invention to solve the technical problem is that an implantable medical device is provided, comprising a metal basal body and a polymer film layer covering the surface of the metal basal body and preventing endothelium growth and covering, at least a part of the surface of the metal basal body is provided with a surface-modified layer which contains doped ions, and the metal basal body is bonded to the polymer film layer by the doped ions.

According to an implanted medical device of an embodiment of the present invention, the doped ions include at least one of oxygen ions, hydroxide ions, carbon ions, nitrogen ions and carbon-nitrogen ions.

According to an implanted medical device of an embodiment of the present invention, a thickness of the surface-modified layer is less than 4 μm.

According to an implanted medical device of an embodiment of the present invention, a thickness of the surface-modified layer is 2 nm-1 μm.

According to an implanted medical device of on embodiment of the present invention, the doped ions are chemically bonded to carbon atoms in the polymer film layer.

According to an implanted medical device of an embodiment of the present invention, the doped ions are chemically bonded to metal elements in the metal basal body; or the doped ions are located in a lattice spacing of the metal basal body.

According to an implanted medical device of an embodiment of the present invention, the polymer film layer comprises at least one of a polyethylene glycol-like polymer, a polyoxyethylene-like polymer, a polyethylene glycol-like derivative, and a polyoxyethylene-like derivative.

According to an implanted medical device of an embodiment of the present invention, the metal basal body comprises at least one of cobalt, chromium, iron, nickel, molybdenum, titanium, platinum and tantalum.

The present invention also provides a method of preparing an implantable medical device, comprising modifying at least a part of a surface of a metal basal body to form a surface-modified layer which contains doped ions, and bonding the metal basal body to the polymer film layer by the doped ions.

In a method of preparing the implanted medical device according to an embodiment of the present invention, the doped ions comprise at least one of oxygen ions, hydroxide ions, carbon ions, nitrogen ions and carbon nitrogen ions.

In a method of preparing the implanted medical device according to an embodiment of the present invention, the modification to at least a part of a surface of a metal basal body to form a surface-modified layer comprises soaking the metal basal body in a soaking solution for soaking reaction to form a surface-modified layer.

In a method of preparing the implanted medical device according to an embodiment of the present invention, the doped ions comprise at least one of oxygen ions and hydroxide ions.

In a method of preparing the implanted medical device according to an embodiment of the present invention, the soaking solution comprises a hydrogen peroxide solution, a mixed solution of a hydrogen peroxide solution and an alkaline solution, a mixed solution of a hydrogen peroxide solution and an acidic solution, and an alkaline solution.

In a method of preparing the implanted medical device according to an embodiment of the present invention, the metal basal body is placed in the different soaking solutions for at least two soaking reactions to form the surface-modified layer.

In a method of preparing the implanted medical device according to an embodiment of the present invention, the soaking solution comprises a hydrogen peroxide solution, a mixed solution of a hydrogen peroxide solution and an alkaline solution, a mixed solution of a hydrogen peroxide solution and an acidic solution, an acidic solution, and an alkaline solution.

In a method of preparing the implanted medical device according to an embodiment of the present invention, when the soaking solution comprises the acidic solution, the acidic solution comprises at least one of an HF solution, an HCl solution, an $H_2SO_4$ solution, an $HNO_3$ solution, an $H_3PO_4$ solution, an $HClO_4$ solution, an HBr solution, an HI solution, an HCN solution, an $H_2SO_3$ solution, an $HNO_2$ solution, a $CH_3COOH$ solution, and an $H_2SeO_4$ solution. The alkaline solution includes at least one of an NaOH solution, an $NaHCO_3$ solution, a KOH solution, a $Ca(OH)_2$ solution, an $NaCO_3$ solution, an $NH_3.H_2O$ solution, an $NH_4HCO_3$ solution and a $K_2CO_3$ solution.

In a method of preparing the implanted medical device according to an embodiment of the present invention, the modification to at least a part of a surface of a metal basal body to form a surface-modified layer comprises injecting the doped ions into the surface of the metal basal body to form the surface-modified layer by a plasma injection method.

In a method of preparing the implanted medical device according to an embodiment of the present invention, the doped ions comprise at least one of an oxygen ion and a nitrogen ion.

In a method of preparing the implanted medical device according to an embodiment of the present invention, the modification to at least a part of a surface of a metal basal body to form a surface-modified layer comprises injecting the doped ions into the surface of the metal basal body to form the surface-modified layer by an ion injection method.

In a method of preparing the implanted medical device according to an embodiment of the present invention, the doped ions comprise at least one of carbon ions, nitrogen ions and carbon-nitrogen ions.

The present invention also provides an implantable medical device preform, comprising a metal basal body, at least a part of which is provided thereon with a surface-modified layer containing doped ions.

According to an implantable medical device preform of an embodiment of the present invention, the doped ions are bonded to carbon atoms in the polymer.

According to an implantable medical device preform of an embodiment of the present invention, the doped ions comprise at least one of oxygen ions, hydroxide ions, carbon ions, nitrogen ions and carbon-nitrogen ions.

According to an implantable medical device preform of an embodiment of the present invention, a thickness of the surface-modified layer is less than 4 μm.

According to an implantable medical device preform of an embodiment of the present invention, a thickness of the surface-modified layer is 2 nm-1 μm.

According to an implantable medical device preform of an embodiment of the present invention, the metal basal body comprises at least one of cobalt, chromium, iron, nickel, molybdenum, titanium, platinum and tantalum.

In an implantable medical device and preparation method thereof according to an embodiment of the present invention, and an implanted medical device preform for preparing the above implanted medical device, at least a part of the metal basal body has a surface-modified layer containing the doped ions, the metal basal body may be bonded to the polymer film layer by the doped ions, so that the polymer film layer will not easily fall off or separate during delivery, so as to effectively play a role of preventing endothelium growth and covering in vivo.

BRIEF DESCRIPTION OF THE DRAWINGS

The present invention will be further described in detail in combination with the accompanying drawings and specific embodiments. In the drawings.

DETAILED DESCRIPTION OF THE INVENTION

In order to provide a clearer understanding of the technical features, objects and effects of the present invention, the embodiments of the present invention will now be described in detail with reference to the drawings. It will be understood by those skilled in the art that taking the filter as an example is not construed as limiting the present invention, and any other implantable medical devices (e.g., lumen stents and occluders) will fall within the scope of protection of the present invention as long as they are based on the teachings of the present invention.

Figure 1:
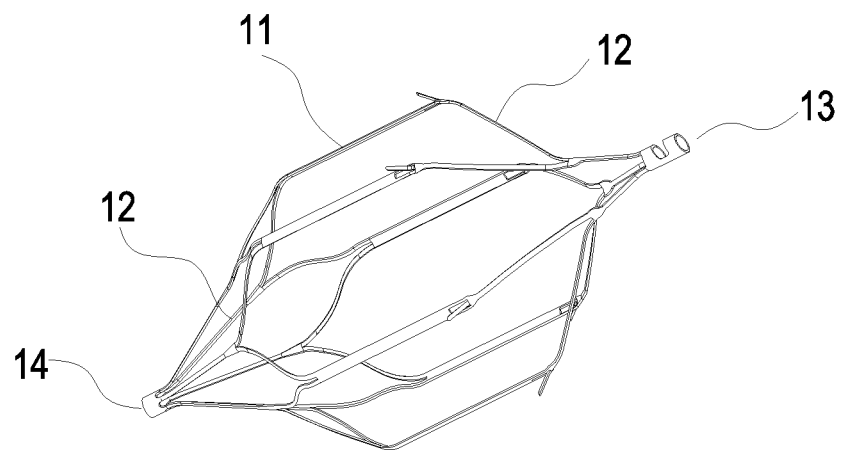
FIG. 1 is a structural schematic diagram of an implantable medical device according to an embodiment of the present invention.

As shown in FIG. 1, at least a part of an implantable medical device 1 (for example, a filter) according to an embodiment of the present invention is required to be in direct contact with the blood vessel wall after the device is implanted into the body. For example, the filter in FIG. 1 includes a plurality of support rods 11 and a plurality of connecting rods 12 provided on both sides of the support rods 11, each supporting rod 11 being uniformly and circumferentially distributed, one end of each of the plurality of connecting rods 12 is connected to the supporting rod 11 and the other end is converged to form a Y-shaped structure and finally form a proximal end 13 or a distal end 14. After radial deployment, the above supporting rods 11 are in direct contact with the blood vessel wall, and provides stable positioning for the filter 1 in the blood vessel through the radial support force to avoid displacement thereof. The support rod 11 is also provided thereon with an anchor to penetrate into the blood vessel wall for locating the filter. Of course, the structure as shown in the figures are for illustrative purposes only and are not construed to be limiting the present invention. The filter may be embodied in different structures. For example, a connecting rod may be provided only on one side of the supporting rod, one end of each connecting rod is connected to the supporting rod, the other ends of the connecting rods converge to form a distal end, and the other side of the supporting rod is an open structure.

Figure 2:
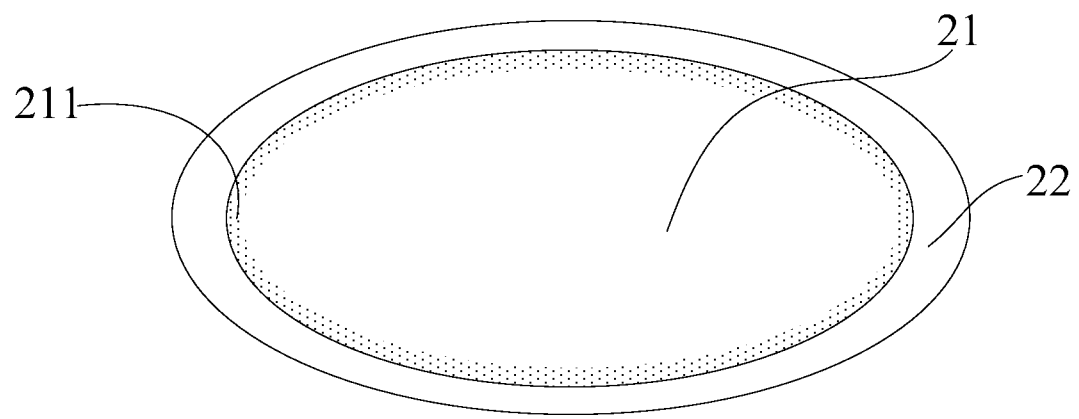
FIG. 2 is a schematic cross-sectional view of the portion of the medical device of FIG. 1 that comes in contact with the blood vessel wall.

With reference to FIG. 2, in an implanted medical device, at least a portion in contact with the blood vessel wall (e.g., the support rod 11 in FIG. 1) comprises a metal basal body 21 and a polymer film layer 22 covering the metal basal body 21 and preventing endothelium growth and covering. The portion of the metal basal body 21 has a surface-modified layer 211 containing doped ions, and the metal basal body 21 is bound to the polymer film layer 22 by the doped ions. The portion of the implanted medical device that is not in contact with the blood vessel wall, for example, the connecting rod 12 in FIG. 1, may have the same structure as the support rod 11 or may be a metal base 21 having no surface-modified layer, or may be a polymer film layer 22 directly covering the metal basal body 21 having no surface-modified layer.

With the structure unchanged, the implanted medical device may also be described as follows: the implanted medical device includes an implanted medical device preform and a polymer film layer covering the preform, the preform comprising a metal basal body, with at least a part of the metal basal body having a surface-modified layer containing doped ions, and the doped ions in the metal basal body may be bonded to the carbon atoms in the polymer.

The metal basal body (hereinafter referred to as "basal body") may be prepared from one of 316L stainless steel nickel titanium alloy, metal titanium, Phynox alloy (cobalt, chromium, iron, nickel, molybdenum alloy), or tantalum alloy having better biocompatibility. The basal body may be prepared by designing the structure of the basal body or using a memory alloy material (e.g., nickel-titanium alloy), so that the basal body has a radially compressed state and a radially expanded state. The basal body may be compressed radially and pushed into the sheath, and then delivered to the predetermined location, such as in a vascular lumen through the sheath. The basal body is released from the sheath of the delivery system and may be restored to a radially expanded state, and pressed to the inner wall of the lumen to be fixed within the lumen. The metal basal body can block and retain thrombosis after being implanted into the lumen, in order to filter the thrombosis.

The surface-modified layer is the outermost surface of the metal basal body and has a thickness of less than 4 μm, usually 2 nm-1 μm. The doped ions in the surface-modified layer include at least one of oxygen ions, hydroxide ions, carbon ions, nitrogen ions and carbon-titanium ions, which may be directly bonded with a metal element Me (Me includes but is not limited to metal elements such as cobalt, chromium, iron, nickel, molybdenum, titanium, platinum and tantalum, which may include one or more metal elements) in the metal basal body, for example, forming one or more Me—O bonds, Me—OH bonds, Me—C bonds, Me—N bonds, and Me—CN bonds; or may be located in the lattice spacing of the metal basal body to form an interstitial.

The concentration of the doped ions is gradually reduced from the surface of the metal basal body to the inside of the metal basal body, and the concentration is the highest at the outermost surface of the metal basal body. The doped ions at the outer surface of the surface-modified layer have no proximal atoms on the outward side of the surface, so that the doped ions at the surface have a part of the chemical bonds extending into the space to form dangling bonds. When the metal basal body is covered with a polymer film layer, the dangling bonds will readily be chemically bonded to the ions/atoms in the polymer film layer.

In particular, the thickness of the polymer film layer is typically less than 3 microns, and the polymer film layer may be at least one of a polyethylene glycol-like polymer, a polyoxyethylene-like polymer, a polyethylene glycol-like derivative, and a polyoxyethylene-like derivative. Specifically, it may be at least one of polyethylene glycol (PEG), polyethylene glycol-like (PEG-like), polyethylene diether, crown ether (e.g., 12-crown ether-4), polyethylene diether-like, polyvinyl alcohol, polyvinyl ether, polyoxyethylene (PEO), polyoxyethylene glycol, polyoxyethylene ether, polyoxyethylene glycol-like, and polyoxyethylene ether-like. The polymer film layer covered on the outermost surface of the medical device can significantly improve the hydrophilicity of the surface of the device, reduce roughness, and can greatly reduce adsorption of bacteria and protein on the surface of the material, and prevent endothelium growth and covering, and increase anticoagulation of the material.

The polymer film layer is rich in carbon atoms. When the polymer film layer covers the metal basal body and is in direct contact with the metal basal body, it is easy for the doped ions (such as oxygen ions, hydroxide ions, carbon ions, nitrogen ions, carbon and nitrogen ions) to be chemically bonded directly to the carbon atoms in the polymer film layer. The dangling bonds of the doped ions at the outer surface of the metal basal body are bonded to the carbon atoms in the polymer film layer to form at least one of C—C bonds, C—C bonds, C=O bonds, C—OH bonds, C—N bonds, C—CN bonds and other chemical bonds, such that the polymer film layer is connected to the metal basal body through the chemical bonds (e.g., covalent bonds). The bonding energy of the chemical bonds is 0.5-10 eV, which is far greater than that of 0.1-0.5 eV between the van der Waals. Therefore, it is difficult to separate the metal basal body from the polymer film layer under the same external force, and the metal basal body may be firmly bonded to the polymer film layer so that the polymer film layer is firmly and effectively attached to the metal basal body.

After the filter according to the present invention is implanted into the lumen, due to the fact that the polymer film layer may be firmly and effectively bonded to the metal basal body by the doped ions, the possibility of the polymer film layer separating when the filter enters and exits the sheath and after the filter is implanted into the lumen will be minimized, and the polymer film layer can function effectively to improve the performance of preventing endothelium growth and covering of the filter.

Figure 3:
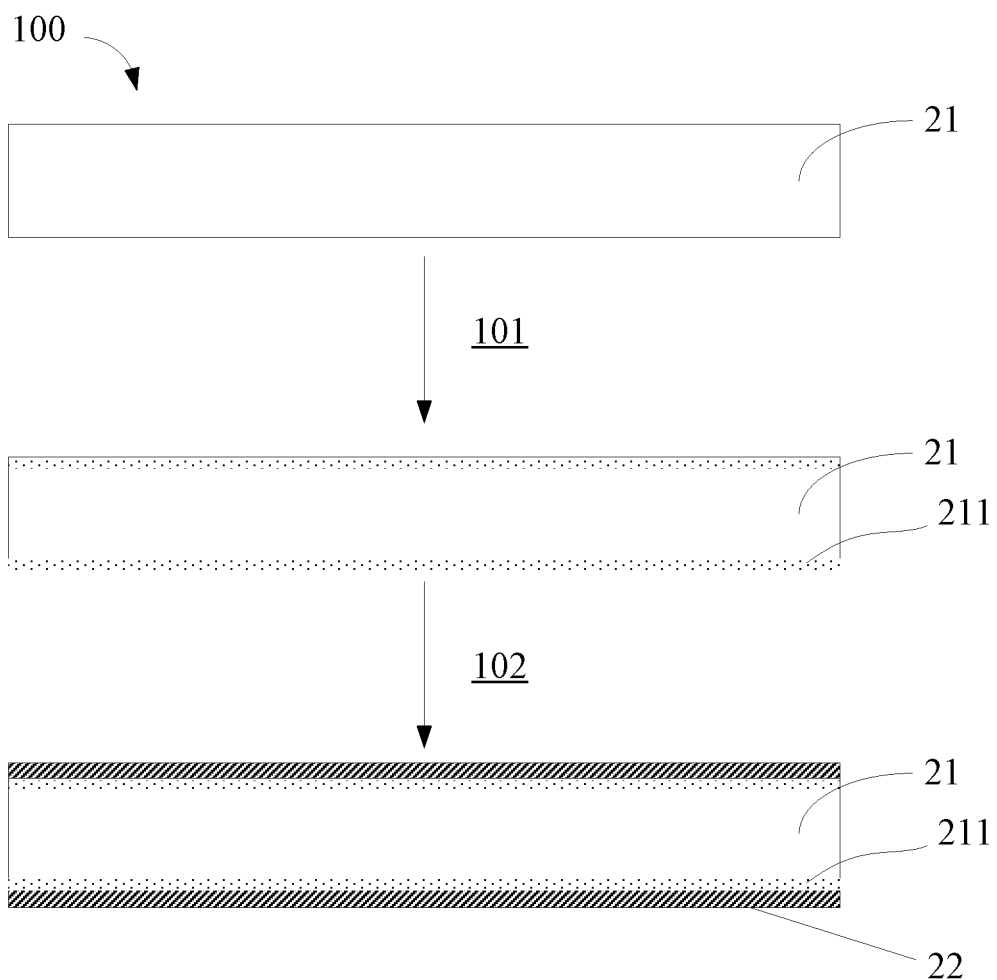
FIG. 3 is a schematic flow chart of a method of preparing an implantable medical device according to an embodiment of the present invention.

FIG. 3 is a schematic flow chart of a preparation method 100 for an implantable medical device (taking a filter as an example) according to an embodiment of the present invention. As shown in FIG. 3, in step 101, modification to at least a part of a surface of a metal basal body to form a surface-modified layer will form an implanted medical device preform. The surface-modified layer has a thickness of less than 4 μm, usually 2 nm-1 μm, and contains doped ions including at least one of oxygen ions, hydroxide ions, carbon ions, nitrogen ions and carbon-nitrogen ions. The concentration of the doped ions is gradually reduced from the surface of the metal basal body to the inside of the metal basal body, and is the highest at the outer surface. The doped ions at the surface have a part of the chemical bonds extending into space to form dangling bonds which are easily bonded to other ions/atoms to form new chemical bonds, so that the metal basal body may be connected to the polymer film layer by doped ions.

The metal basal body may be subjected to surface modification by chemical surface treatment to form a surface-modified layer. Specifically, the metal basal body may be placed in a soaking solution, and forms a surface-modified layer on the surface through chemical reaction with the soaking solution. Surface modification may be performed by soaking reaction once in only one soaking solution, and the optional soaking solutions include a hydrogen peroxide solution, a mixed solution of a hydrogen peroxide solution and an alkaline solution, a mixed solution of a hydrogen peroxide solution and an acidic solution, and an alkaline solution. When in reaction, the temperature of the soaking solution may be room temperature, or the soaking solution can also be heated at high temperature or even to boiling temperature. Surface modification may be performed by soaking reaction for many times in numerous soaking solutions, and the soaking solutions used at present include a hydrogen peroxide solution, a mixed solution of a hydrogen peroxide solution and an alkaline solution, a mixed solution of a hydrogen peroxide solution and an acidic solution, and an acidic solution or an alkaline solution. The acidic solution can include at least one of an HF solution, an HCl solution, an $H_2SO_4$ solution, an $HNO_3$ solution, an $H_3PO_4$ solution, an $HClO_4$ solution, an HBr solution, an HI solution, an HCN solution, an $H_2SO_3$ solution, an $HNO_2$ solution, a $CH_3COOH$ solution, and an $H_2SeO_4$ solution; a same alkaline solution may be used in the above two reaction processes, which includes at least one of an NaOH solution, an $NaHCO_3$ solution, a KOH solution, a $Ca(OH)_2$ solution, an $Na_2CO_3$ solution, an $NH_3.H_2O$ solution, an $NH_4HCO_3$ solution and a $K_2CO_3$ solution.

For example, the original metal basal body may be subjected to soaking reaction in an $H_2O_2$ solution or a boiling solution containing hydrogen peroxide to form a surface-modified layer containing Me—O and Me—OH bonds on the surface of the metal or alloy. The soaking solution may also be a mixed solution of hydrogen peroxide and an alkaline solution, and a surface-modified layer containing Me—O and Me—OH bonds is formed on the surface of the metal basal body after the soaking reaction. It is also possible to subject the original metal basal body in a hydrogen peroxide solution first to form a surface-modified layer containing Me—O and Me—OH bonds; and then in an alkaline solution for a secondary soaking reaction, and further forming Me—O and Me—OH bonds in the surface-modified layer. Similarly, the original metal basal body may be placed in an acidic solution first for soaking reaction to activate the surface of the metal basal body; and then in a boiling alkaline solution for a secondary soaking reaction, and further forming Me—C and Me—OH bonds in the surface-modified layer.

The surface-modified layer comprising Me—O and/or Me—OH bonds may be formed on the surface of the metal basal body by the soaking reaction as above, and the oxygen ions and the hydroxide ions located at the outer surface of the surface-modified layer may be chemically bonded to the carbon atoms in the polymer directly to form at least one of C—O, C—OH and C═O bonds, thereby firmly bonding the metal basal body to the polymer film layer so that the polymer film layer is unlikely to separate from the metal basal body.

The surface-modified layer may be formed by injecting the doped ions into the surface of the metal basal body by a plasma injection method. For example, the original metal basal body is placed in a vacuum apparatus at a preset degree of vacuum and under an oxygen or nitrogen atmosphere, and the glow discharge power source is turned on to produce an oxygen plasma or nitrogen plasma, a highly reactive oxygen plasma or a nitrogen plasma reacts with the metal to form an Me—O or Me—N bond on the surface of the metal basal body, thus forming a surface-modified layer containing Me—O or Me—N bonds. The oxygen ions and nitrogen ions located at the outer surface of the surface-modified layer may be chemically bonded to the carbon atoms in the polymer directly to form at least one of C—O, C═O and C—N bonds, thereby firmly bonding the metal basal body to the polymer film layer, so that the polymer film layer cannot easily separate from the metal basal body.

The surface-modified layer may be formed by injecting the doped ions into the surface of the metal basal body by an ion injection method. For example, the original metal basal body may be placed in a high-energy ion injection apparatus for injection of the doped ions, specifically, at a preset degree of vacuum, the electrons generated by a hot filament (commonly used tungsten filament) source is used for bombarding the gas molecules or atoms, or solid targets to be injected, and the bombarded particles (gas molecules or atoms, or solid targets) are ionized to form ions. Charged ions in the magnetic field have movement trajectory deflected by Lorentz force to sort out required ions; the ions are accelerated to obtain required energy with a strong electric field of the accelerator. Finally, ions are injected into the surface of the metal basal body by focusing lenses and beam scanning devices.

With this method, at least one of a carbon ion, a nitrogen ion and a carbon-nitrogen ion may be injected into the surface of the metal basal body to form a surface-modified layer. For example, nitrogen may be used as a bombarded gas to inject N-elements into the surface of the metal basal body to form Me—N bonds; C ions may be produced with methane, acetylene and other hydrocarbon gases being used as a carbon source, and C elements are injected into the surface of the metal basal body to form Me—C bonds; a mixed gas of a nitrogen gas, a methane, an acetylene and other hydrocarbon gases may be used simultaneously to inject C and N elements into the surface of the metal basal body to form Me—CN bonds; graphite may be used as a carbon source to inject C elements into the surface of the metal basal body, make the graphite into a target, and C ion beams are formed after electron bombardment, then the C ion beams are injected into the surface of the metal basal body to form Me—C bonds.

At least one of carbon ions, nitrogen ions and carbon-nitrogen ions located at the outer surface of the surface-modified layer may be chemically bonded directly to the carbon atoms in the polymer to form at least one of C—N, C—C and C—CN bonds, thereby firmly connecting the metal basal body with the polymer film layer, so that the polymer film layer is unlikely to separate from the metal basal body.

Of course, the doped ions cannot only be directly bonded with the metal elements in the metal basal body, but also in the lattice spacing of the metal basal body to form interstitials. Taking C doped ions as an example, the C ions in the surface-modified layer can form Me—C bonds with the metal elements or are in the lattice spacing of the metal basal body.

In step 102, the surface of the metal basal body having the surface-modified layer in step 101 is coated with the polymer film layer so as to bond the metal basal body and the polymer film layer by the doped ions contained in the surface-modified layer.

A polymer film layer may be covered on the surface of the transition body and the surface of the metal basal body by chemical vapor deposition method (e.g., radio frequency plasma enhanced chemical vapor deposition RF-PECVD and microwave electron cyclotron resonance plasma chemical vapor deposition ECR-CVD). The prepared polymer film layer may be at least one of a polyethylene glycol-like polymer, a polyoxyethylene-like polymer, a polyethylene glycol-like derivative, and a polyoxyethylene-like derivative. Specifically, it may be at least one of polyethylene glycol, polyethylene glycol-like, polyethylene diether, crown ether, polyethylene diether-like, polyvinyl alcohol, polyvinyl ether, polyoxyethylene, polyoxyethylene glycol, polyoxyethylene ether, polyoxyethylene glycol-like, and polyoxyethylene ether-like.

For example, in the process of preparing a polymer film layer by chemical vapor deposition, the monomer molecules may be ionized and reacted to form a polymer film layer coated metal basal body, wherein the monomer molecule comprises at least one of ethylene glycol, diethylene glycol, ethylene glycol dimethyl ether, diethylene glycol dimethyl ether, triethylene glycol dimethyl ether, and tetraethylene glycol dimethyl ether.

In order to further improve the performance of the filter, the metal basal body may also be cleaned prior to step 101. For example, the metal basal body may be placed in the same apparatus as in step 102, and the metal basal body is subjected to plasma cleaning under vacuum conditions. In addition, the metal basal body may be first subjected to ultrasonic cleaning.

Example 1

Prior to step 101, the original metal basal body was first subjected to plasma cleaning, the original metal basal body was placed on a sample rack in a vacuum chamber which was vacuumized below 10 Pa, and an argon gas having a flow rate of 20-200 sccm was passed to keep the pressure of the vacuum chamber below 10 Pa; the surface of the original metal basal body was subjected to plasma cleaning for 5 to 60 min under the condition of RF plasma power being 50-1000 W and bias voltage being 10-800 V, and then the radio-frequency power supply was turned off and the original metal basal body was removed. Or the original metal basal body may be subjected to ultrasonic cleaning, the original metal basal body then placed into a container with ethanol, acetone or other cleaning agents, and then the container was placed in an ultrasonic cleaning tank for ultrasonic cleaning for 5 to 30 min, the original metal basal body then being removed and blow-dried using compressed air or hot air.

In step 101, the cleaned original metal basal body was subjected to a soaking reaction using a hydrogen peroxide solution as a soaking solution. Concentration of $H_2O_2$ in the solution was 10-35 wt %, the time for soaking reaction was 1-180 min, the original metal basal body was removed after the soaking reaction, subjected to ultrasonic cleaning with distilled water for 5-30 min, and blow-dried with hot air or purified compressed air to obtain a metal basal body having a surface-modified layer containing Me—O and Me—OH bonds.

In step 102, a polymer film layer (a PEG-like film layer) was coated on the outermost layer of the surface of the metal basal body, and a radio frequency plasma enhanced chemical vapor deposition (RF-PECVD) method was used in the present embodiment. Specifically, argon was introduced at a flow rate of 10-100 sccm to control the atmospheric pressure in the reaction chamber to be 2-7 Pa, which was 1-2 Pa lower than the pressure set in the reaction deposition. A needle valve of a heated (heating temperature was set to 80-150° C.) triethylene glycol dimethyl ether reaction cylinder was opened to adjust the pressure of the vacuum chamber to the deposition set pressure, and the reaction deposition pressure was set to 3-9 Pa; the radio frequency power supply was adjusted to 20-200 W, bias voltage of 10-200 V, and the deposition time under the above conditions was 10-60 min. After that, all the reaction gases, RF power supplies and bias voltages were cut off, the vacuum pump was closed, and the finished filter product was removed.

The schematic cross-section of the filter prepared in Example 1 is similar to that of FIG. 2, and the surface of the metal basal body 21 of the filter was coated with a PEG-like film layer 22 to prevent endothelium growth and covering; the surface-modified layer 211 of the metal basal body 21 was in direct contact with the PEG-like film layer 22, oxygen ions and hydroxide ions with dangling bonds were contained in the thickness of the atomic layers of the outermost layer of the surface-modified layer 211, the oxygen ions and hydroxide ions were easily bonded to the carbon atoms in the PEG-like film layer 22 to form at least one of C—O, C=O and C—OH chemical bonds through which the metal basal body 21 may be bonded to the PEG-like film layer 22 firmly and would not easily separate.

Example 2

The difference from Example 1 is as follows: in step 101 of the example, a mixed solution of an $H_2O_2$ solution and an NaOH solution was used as a soaking solution in which the weight concentration of $H_2O_2$ was 10-35% and the weight concentration of the alkaline substance was 5-35%, and the time for the soaking reaction is 1-180 min. After the soaking reaction, the metal basal body was removed, ultrasonic cleaned with distilled water for 5 to 30 min, and finally was dried at room temperature to obtain a metal basal body having a surface-modified layer containing Me—O and Me—OH bonds. The oxygen ions and the hydroxide ions in the surface-modified layer were bonded to the carbon atoms in the polymer film layer to form at least one of C—O, C=O and C—OH chemical bonds through which the metal basal body could be firmly bonded with the polymer film layer and would not easily separate.

Example 3

The difference from Example 1 is as follows: the original metal basal body was subjected to two soaking reactions using two different soaking solutions in step 101 of the example. An $H_2O_2$ solution having a weight concentration of 10-35% was used as a soaking solution for the first soaking reaction, and the time for the soaking reaction was 1-60 min. A mixed solution of an NaOH solution and a KOH solution having a weight concentration of 5-35% of the alkaline substance was used for the second soaking reaction, and the reaction soaking time was 1-180 min. The metal basal body was removed after the soaking reaction, washed and dried to obtain a metal basal body having a surface-modified layer containing Me—O bonds and Me—OH bonds. The oxygen ions and the hydroxide ions in the surface-modified layer were bonded to the carbon atoms in the polymer film layer to form at least one of C—O, C=O and C—OH chemical bonds through which the metal basal body could be firmly bonded with the polymer film layer and would not easily separate.

Example 4

The difference from Example 1 is as follows: the original metal basal body was subjected to two soaking reactions using two different soaking solutions in step 101 of the example. A mixed solution of HF acid having a weight concentration of 1-50% and a nitric acid having a molar concentration of 0.1-8 mol/L was used as a soaking solution for the first soaking reaction for 0.5-10 min; an NaOH strong base solution having a weight concentration of 5-35% was used as a soaking solution for the second soaking reaction for 1-180 min. The metal basal body was removed after the soaking reaction, washed and blow-dried with hot air or purified compressed air to obtain a metal basal body having a surface-modified layer containing Me—O bonds and Me—OH bonds. The oxygen ions and the hydroxide ions in the surface-modified layer were bonded to the carbon atoms in the polymer film layer to form at least one of C—O, C=O and C—OH chemical bonds through which the metal basal body could be firmly bonded with the polymer film layer and would not easily separate.

Example 5

The difference from Example 1 is as follows: a mixed solution of an $H_2SO_4$ solution having a molar concentration of 0.1-5 mol/L and an $H_2O_2$ solution having a molar concentration of 0.1-9 mol/L was used as a soaking solution in step 101 of the example, and the time for the soaking reaction was 0.5-20 min. The metal basal body was removed after the soaking reaction, washed and dried to obtain a metal basal body having a surface-modified layer containing Me—O bonds and Me—OH bonds. The oxygen ions and the hydroxide ions in the surface-modified layer were bonded to the carbon atoms in the polymer film layer to form at least one of C—O, C=O and C—OH chemical bonds through which the metal basal body could be firmly bonded with the polymer film layer and would not easily separate.

Example 6

The difference from Example 1 is as follows: in step 101 of the example, a plasma injection method was used to inject the doped ions into the original metal basal body to form a surface-modified layer on the surface of the metal basal body. In implementation, the original metal basal body was placed on a sample rack in a vacuum chamber which was vacuumed below 10.0 Pa; a mixed gas of argon and oxygen was introduced, with the flow rate of argon being 10-100 sccm, the flow rate of the oxygen being 20-200 sccm, and the oxygen with a flow rate of 20-200 sccm can also be used alone, such that the pressure of the vacuum chamber may be kept below 20.0 Pa, the radio frequency plasma power supply was turned on, the surface of the original metal basal body was subjected to oxygen plasma injection for 5-60 min under the conditions that the power was 10-1000 W, and the bias voltage was 10-800 V. A metal basal body having a surface-modified layer containing Me—O bonds was obtained. The oxygen ions in the surface-modified layer were easily bonded to the carbon atoms in the polymer film layer to form at least one of C—O, C=O through which the metal basal body could be firmly bonded with the polymer film layer and would not easily separate.

Example 7

The difference from Example 6 is as follows: a surface-modified layer was formed on the surface of the metal basal body by nitrogen plasma injection in step 101. Specifically, the original metal basal body was placed on a sample rack in a vacuum chamber which was vacuumed below 10.0 Pa, a mixed gas of argon and nitrogen was introduced, with the flow rate of argon being 10-100 sccm, the flow rate of the nitrogen being 20-200 sccm, and the nitrogen with a flow rate of 20-200 sccm can also be used alone, such that the pressure of the vacuum chamber may be kept below 20.0 Pa; the radio frequency plasma power supply was turned on, the basal body of the original metal basal body was subjected to nitrogen plasma injection for 5-60 min under the conditions that the power was 10-1000 W, and the bias voltage was 10-800 V. A metal basal body having a surface-modified layer containing Me—N bonds was obtained. The nitrogen ions in the surface-modified layer may be easily bonded to the carbon atoms in the polymer film layer to form C—N chemical bonds through which the metal basal body could be firmly bonded with the polymer film layer and would not easily separate.

Example 8

The difference from Example 1 is as follows: in step 101 of the example, a plasma injection method was used to inject the doped ions into the original metal basal body to form a surface-modified layer on the surface of the metal basal body. In implementation, the original metal basal body was placed on a sample rack in a vacuum chamber of the ion injection apparatus, and the vacuum chamber was vacuumed below $1\times10^{-4}$ Pa; and nitrogen gas of 5-50 sccm was introduced to keep the vacuum below $1\times10^{-3}$ Pa; the ion injection power supply was turned on, ion injection energy was set to 10-500 keV, and the injection time was 3-60 min. A metal basal body having a surface-modified layer containing Me—N bonds was obtained. The nitrogen ions in the surface-modified layer may be easily bonded to the carbon atoms in the polymer film layer to form C—N chemical bonds through which the metal basal body could be firmly bonded with the polymer film layer and would not easily separate.

Example 9

The difference from Example 8 is as follows: the original metal basal body was placed on a sample rack in a vacuum chamber of the ion injection apparatus, and the vacuum chamber was vacuumed below $1\times10^{-4}$ Pa; and methane gas of 5-50 sccm was introduced to keep the vacuum below $1\times10^{-3}$ Pa; the ion injection power supply was turned on, ion injection energy was set to 10-500 keV, and the injection time was 3-60 min. A metal basal body having a surface-modified layer containing Me—C bonds was obtained. The nitrogen ions in the surface-modified layer may be easily bonded to the carbon atoms in the polymer film layer to form C—C chemical bonds through which the metal basal body could be firmly bonded with the polymer film layer and would not easily separate.

Example 10

The difference from Example 8 is as follows: the original metal basal body was placed on a sample rack in a vacuum chamber of the ion injection apparatus, and the vacuum chamber was vacuumed below $1\times10^{-4}$ Pa, and a high purity graphite target was used as a carbon source; the ion injection power supply was turned on, ion injection energy was set to 10-500 keV, and the injection time was 3-60 min. A metal basal body having a surface-modified layer was obtained, with a part of the injected carbon elements of the surface-modified layer forming Me—C bonds with the metal elements Me, and a part of the injected carbon elements was used as an interstitial in the lattice spacing of the metal basal body. Therefore, a metal basal body having a surface-modified layer was obtained, the carbon ions in the surface-modified layer were easily bonded to the carbon atoms in the polymer film layer to form C—C chemical bonds through which the metal basal body may be bonded to the polymer film layer firmly, and would not easily separate.

Example 11

The difference from Example 8 is as follows: the original metal basal body was placed on a sample rack in a vacuum chamber of the ion injection apparatus, and the vacuum chamber was vacuumed below $1\times10^{-4}$ Pa, and a nitrogen gas of 2-30 sccm and a methane gas of 4-60 sccm were introduced, the vacuum chamber was kept below $1\times10^{-3}$ Pa; the injection power supply was turned on, the ion injection energy was set to 10-500 keV, and the injection time was 3-60 min. A metal basal body having a surface-modified layer was obtained. The carbon ions and nitrogen ions in the surface-modified layer may be easily bonded to the carbon atoms in the polymer film layer to form at least one of C—C and C—N chemical bonds through which the metal basal body could be firmly bonded with the polymer film layer and would not easily separate.

As can be seen from the above, in the preparation method of the implanted device of the present invention, the metal basal body was first subjected to surface modification to form a surface-modified layer, and the metal basal body was coated with a polymer film layer which prevents endothelium growth and covering. In the implanted device prepared as above, the doped ions in the surface-modified layer may be bonded to the carbon atoms in the polymer film layer to form at least one of C—C bonds, C—O bonds, C—OH bonds, C—N bonds, C—CN, etc. The bonding energy of the chemical bonds could be far greater than the bonding energy and mechanical binding energy between the molecules, so that the polymer film layer may be firmly bonded to the metal basal body. Thus, the polymer film layer may be firmly bonded to the metal basal body with the doped ions as a medium, so that the polymer film layer on the surface of the resulting filter would not easily separate and fall off when the resulting filter is inserted into and is pulled out of the sheath and implanted.

The above specific embodiments are only used for illustrative purposes and not intended to limit the present invention. Those skilled in the art will be able to prepare a filter in any suitable manner based on the teachings of the present invention, and the prepared filter has characteristics such as the polymer film would not easily separate or fall off, the performance of preventing endothelium growth and covering is good, and the time window for safe removal of the filter is long.

The invention claimed is:

1. An implanted medical device which is either a stent, a filter or an occluder, comprising a metal basal body and a polymer film layer covering a surface of the metal basal body and preventing endothelium growth and covering, wherein at least a part of the surface of the metal basal body is provided with a surface-modified layer which contains doped ions, and the metal basal body is bonded to the polymer film layer by the doped ions;

wherein the doped ions are chemically bonded to carbon atoms in the polymer film layer and comprise at least one of oxygen ions, hydroxide ions, carbon ions, nitrogen ions and carbon-nitrogen ions; and wherein the polymer film layer comprises at least one of a polyethylene glycol-like polymer, a polyoxyethylene-like polymer, a polyethylene glycol-like derivative, and a polyoxyethylene-like derivative.

2. The implanted medical device according to claim 1, characterized in that a thickness of the surface-modified layer is less than 4 µm.

3. The implanted medical device according to claim 1, characterized in that the metal basal body comprises at least one of cobalt, chromium, iron, nickel, molybdenum, titanium, platinum and tantalum.

4. A method of preparing an implanted medical device which is either a stent, a filter or an occluder, comprising the steps of:

modifying at least a part of a surface of a metal basal body to form a surface-modified layer which contains doped ions, and bonding the metal basal body to a polymer film layer by the doped ions; wherein the doped ions are chemically bonded to carbon atoms in the polymer film layer and comprise at least one of oxygen ions, hydroxide ions, carbon ions, nitrogen ions and carbon-nitrogen ions; and wherein the polymer film layer comprises at least one of a polyethylene glycol-like polymer, a polyoxyethylene-like polymer, a polyethylene glycol-like derivative, and a polyoxyethylene-like derivative.

5. The method of preparing an implanted medical device according to claim 4, wherein the modifying step comprises soaking the metal basal body in a soaking solution to form the surface-modified layer.

6. The method of preparing an implanted medical device according to claim 5, characterized in that the soaking solution comprises at least one of a hydrogen peroxide solution, a mixed solution of a hydrogen peroxide solution and an alkaline solution, a mixed solution of a hydrogen peroxide solution and an acidic solution, and an alkaline solution.

7. The method of preparing an implanted medical device according to claim 5, characterized in that the metal basal body is placed in different soaking solutions for at least two soaking reactions to form the surface-modified layer.

8. The method of preparing an implanted medical device according to claim 6, characterized in that when the soaking solution comprises at least one of the acidic solution, the acidic solution comprises at least one of an HF solution, an HCl solution, an $H_2SO_4$ solution, an $HNO_3$ solution, an $H_3PO_4$ solution, an $HClO_4$ solution, an HBr solution, an HI solution, an HCN solution, an $H_2SO_3$ solution, an $HNO_2$ solution, a $CH_3COOH$ solution, and an $H_2SeO_4$ solution; the alkaline solution comprises at least one of an NaOH solution, an $NaHCO_3$ solution, a KOH solution, a $Ca(OH)_2$ solution, an $Na_2CO_3$ solution, an $NH_3.H_2O$ solution, an $NH_4HCO_3$ solution and a $K_2CO_3$ solution.

9. The method of preparing an implanted medical device according to claim 4, wherein the modifying step comprises injecting the doped ions into the surface of the metal basal body to form the surface-modified layer by a plasma injection method.

\* \* \* \* \*